(12) United States Patent
Asotra et al.

(10) Patent No.: US 7,981,435 B2
(45) Date of Patent: *Jul. 19, 2011

(54) SPILL RESISTANT FORMULATIONS CONTAINING CLAYS

(75) Inventors: Satish Asotra, Brampton (CA); Zoltan Bodor, Pickering (CA); Xiaoli Wang, Mississauga (CA)

(73) Assignee: Taro Pharmaceuticals U.S.A. Inc., Hawthorne, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/779,205

(22) Filed: May 13, 2010

(65) Prior Publication Data

US 2010/0222298 A1    Sep. 2, 2010

Related U.S. Application Data

(63) Continuation of application No. 10/975,898, filed on Oct. 28, 2004, now Pat. No. 7,744,908.

(60) Provisional application No. 60/514,999, filed on Oct. 28, 2003.

(51) Int. Cl.
*A61K 9/00* (2006.01)

(52) U.S. Cl. ............... 424/400; 424/401; 424/9.411; 424/435

(58) Field of Classification Search ............... None
See application file for complete search history.

(56) References Cited

U.S. PATENT DOCUMENTS

| | | | |
|---|---|---|---|
| 4,867,979 A | 9/1989 | Sheth et al. | |
| 5,079,001 A | 1/1992 | Affolter | |
| 5,466,440 A | 11/1995 | Ruddy et al. | |
| 5,881,926 A | 3/1999 | Ross | |
| 6,071,523 A | 6/2000 | Mehta et al. | |
| 6,102,254 A | 8/2000 | Ross | |
| 6,224,888 B1 | 5/2001 | Vatter et al. | |
| 6,355,258 B1 | 3/2002 | Mehta | |
| 6,399,079 B1 | 6/2002 | Mehta | |
| 6,509,007 B2 * | 1/2003 | Rajaiah et al. | 424/53 |
| 6,656,482 B2 | 12/2003 | Mehta | |
| 2004/0014823 A1 | 1/2004 | Chaiko | |

FOREIGN PATENT DOCUMENTS

WO    WO 93/08230        4/1993
WO    WO 9308230 A1 *    4/1993

OTHER PUBLICATIONS

Feng, et al., (2003) A novel laponite clay-based Fe nanocomposite and its photo-catalytic activity in photo-assisted degradation of Orange II. Chem. Eng. Sci. 58: 679-685.
Zebrowski, et al., (2003) Shake gels: shear-induced gelation of laponite-PEO mixtures. Colloids and Surfaces A: Physiochem. Eng. Aspects. 213: 189-197.
Rockwood Additives Limited, Laponite, www.rockwoodadditives.com/laponite.htm (accessed Aug. 14, 2003).
International Search Report for PCT/US04/35851.
Written Opinion of the International Searching Authority for PCT/US04/35851.
International Preliminary Report on Patentability for PCT/US04/35851.
"Hydrocolloids," Science Tech Entrepreneur, Feb. 2007.
Remington, The Science and Practice of Pharmacy, 21st Ed., 2005, p. 345.
Laponite XLG, product bulletin, www.gelwhite.com/tb23.html, accessed Aug. 19, 2003.
Sardinha, H. et al., Gel formation in clay solutions: tuning viscoelasticity with added polymer, www.ecs.umass.edu/hamilton/2001/sardinha_heidi.htm, accessed Aug. 19, 2003.
Zebrowski, Shake Gels, www.deas.harvard.edu/projects/weitzlab/research/laponite.html, accessed Aug. 19, 2003.

* cited by examiner

*Primary Examiner* — Sudhakar Katakam

(74) *Attorney, Agent, or Firm* — Venable LLP; Michael A. Gollin; Thomas F. Barry

(57) ABSTRACT

The invention relates to novel spill resistant formulations comprising either a weak base or a weak acid as the pharmaceutical ingredient, a liquid base, a clay and a water soluble cellulose ether. The clay and cellulose ether allow for a broader pH range into which the pharmaceutically active agent may be dispersed or dissolved, and therefore allows for easier preparation and formulation of the pharmaceutical composition.

20 Claims, No Drawings

SPILL RESISTANT FORMULATIONS CONTAINING CLAYS

CROSS-REFERENCE TO RELATED APPLICATIONS

This application is a continuation of U.S. application Ser. No. 10/975,898, filed Oct. 28, 2004, which claims the benefit of U.S. Provisional Application 60/514,999, filed Oct. 28, 2003. Each of these applications is incorporated by reference in its entirety and for all purposes.

BACKGROUND OF THE INVENTION

Syrups, elixirs, solutions, and suspensions are traditional dosage forms for oral medication. These liquid formulations are typically measured by pouring into a spoon, but this approach has the great drawback of spillage. The risk of spillage can cause people to underfill or spill from the spoon, leading to inaccurate dosage. With elderly people, children, and the infirm, lack of motor skills or poor attention can cause difficulty in filling a spoon with a liquid and bringing it to the mouth. This can result in a serious impediment to administering the medicine. Solid formulations such as pills, tablets, and capsules are also difficult for children and for elderly, infirm people to swallow.

Recently, pharmaceutical preparations that are resistant to spilling for the oral delivery of pharmaceutically active agents have been described in the commonly owned U.S. Pat. Nos. 5,881,926, 6,071,523, 6,102,254, 6,355,258, 6,399,079, and 6,656,482 incorporated herein in their entirety by reference. U.S. Pat. Nos. 5,881,926 and 6,102,254 describe a pharmaceutical delivery system for spill resistant formulations. U.S. Pat. Nos. 6,071,523, 6,355,258, 6,399,079 and 6,656,482 describe the spill resistant pharmaceutical compositions in terms of their physico-chemical properties and methods of preparing and using those formulations. These patents describe oral dosage forms for the delivery of active agents that do not spill easily, are organoleptically pleasing and are storage stable.

The previously described spill-resistant pharmaceutical formulation for oral administration are from a squeezable container comprising a per-unit dose effective amount of a pharmaceutical agent in a suitable vehicle comprising a liquid base and a thickening or viscosity agent. In the previously described spill resistant formulations, the thickening or viscosity agent utilized most frequently was carbomer, a synthetic, high molecular weight, polymer of acrylic acid cross-linked with allylsucrose. The viscosity of the carbomer gels are known to be pH dependent. Carbomer gels exhibit maximum viscosity at about neutral pH, where the viscosity plateaus between pH values of 6.3 to 7.0. This pH-viscosity interaction of the carbomer polymer has restricted the use of weak acids and weak bases in spill resistant pharmaceutical formulations. At higher or lower pH ranges, the ranges where the weak acids and bases are most soluble, the formulations lose their spill resistant properties. Now, using clays, we have expanded the pH range available for spill resistant formulations. This enables the development of spill resistant formulations where the pharmaceutical active agents have either acidic or basic pKa's.

SUMMARY OF THE INVENTION

The invention provides for a pharmaceutical formulation, comprising a weakly basic pharmaceutically active ingredient, a liquid base, clay and at least one water soluble cellulose ether, wherein the pharmaceutical formulation exhibits spill resistant characteristics.

The pharmaceutical formulation of the invention which comprises a weakly basic pharmaceutically active ingredient, a liquid base, clay and at least one water soluble cellulose ether, wherein the pharmaceutical formulation exhibits spill resistant characteristics, and the pH of the pharmaceutical formulation is between about 3.0 to about 6.5.

An embodiment of the inventive pharmaceutical formulation is that the composition comprising a weakly basic active ingredient, a liquid base, a clay and at least one water soluble cellulose ether has a viscosity in the range of from about 5,000 cps to about 25,000 cps. A further embodiment of the inventive pharmaceutical formulation is that the composition comprising a weakly basic active ingredient, a liquid base, a clay and one water soluble cellulose ether has a viscosity in the range of from about 5,000 cps to about 12,000 cps.

A further embodiment of the inventive formulation is that the weakly basic pharmaceutically active ingredient, the liquid base, a clay and the water soluble cellulose ether do not separate into separate components after storage at room temperature for at least 24 month. In a further embodiment of the inventive formulation, the weakly basic pharmaceutically active ingredient, the liquid base, the clay and the water soluble cellulose ether do not separate under accelerated stability conditions for at least 6 months.

In a specific embodiment of the invention, the pharmaceutical formulation has a liquid base which is selected from a group consisting of glycerin, propylene glycol or sorbitol or mixtures thereof.

The invention provides for a pharmaceutical formulation comprising a weakly basic pharmaceutically active ingredient, a liquid base, a clay and a water soluble cellulose ether wherein the clay is selected from the group consisting of laponite, bentonite, montmorillonite, beidelite, hectorite, saponite and stevensite, and mixtures thereof.

Further, the inventive formulation comprises a weakly basic pharmaceutically active ingredient, a liquid base, a clay and a water soluble cellulose ether, wherein the clay is laponite.

The pharmaceutical formulation of the invention which comprises a weakly basic pharmaceutically active ingredient, a liquid base, a clay and at least one water soluble cellulose ether, wherein the pharmaceutical formulation exhibits spill resistant characteristics, and the pH of the pharmaceutical formulation is between about 3.0 to about 5.0.

The invention as described includes a weakly basic pharmaceutically active ingredient selected from the group consisting of acyclovir, atenolol, atropine, ciprofloxacin, diltiazem, diphenhydramine, diphenhydramine HCl, epinephrine, ephedrine, glucosamine, glucosamine sulfate, hydrochlorothiazide, metoprolol, nortriptyline, phenytoin, prednisone, propoxyphene, propranolol, terfenadine, tetracycline, pseudoephedrine and mixtures thereof.

More specifically, the inventive pharmaceutical formulation comprises:
  (a) water in amounts from about 20% (w/w) to about 98% (w/w);
  (b) glycerin in amounts from about 20% (w/w) to about 60% (w/w);
  (c) clay in amounts from about 0.25% (w/w) to about 0.5% (w/w);
  (d) water soluble cellulose ethers in amounts from about 0.8% (w/w) to about 2.0% (w/w);
  (e) an effective amount of a pharmaceutically active ingredient.

In another embodiment of the invention, the pharmaceutical formulation includes the water soluble cellulose ether, carboxymethyl cellulose.

In another embodiment of the pharmaceutical formulation of the Invention propylene glycol may be used in the composition. Additionally, the propylene glycol may be used in amounts of about 5% (w/w). Alternatively, sorbitol may be used in the pharmaceutical composition of the invention in amounts of about 5% (w/w).

The invention also provides for a pharmaceutical formulation, comprising a weakly acidic pharmaceutically active ingredient, a liquid base, clay and at least one water soluble cellulose ether, wherein the pharmaceutical formulation exhibits spill resistant characteristics.

Furthermore, the pharmaceutical formulation comprising a weakly acidic pharmaceutically active ingredient, a liquid base, a clay and at least one water soluble cellulose ethers, wherein the formulation may have a pH of between about 7.5 to about 10.

The invention provides for a pharmaceutical formulation comprising a weakly acidic pharmaceutically active ingredient, a liquid base, a clay and at least one water soluble cellulose ether, wherein the viscosity ranges from about 5,000 cps to about 25,000 cps. In a further embodiment, the viscosity ranges from about 5,000 to 12,000 cps.

In a further embodiment, the weakly acidic pharmaceutically active ingredient, the liquid base, the clay and the water soluble cellulose ether pharmaceutical formulation will not separate into separate components after storage at room temperature for at least 24 months. Additionally, the pharmaceutical formulation will not separate under accelerated stability conditions for at least 6 months.

The pharmaceutical formulation of comprising a weakly acidic pharmaceutically active ingredient, a liquid base, clay and a water soluble cellulose ethers wherein the liquid base is selected from a group consisting of glycerin, propylene glycol or sorbitol.

Additionally, the pharmaceutical formulation comprising a weakly acidic pharmaceutically active ingredient, a liquid base, a clay and a water soluble cellulose ethers, wherein the clay is selected from the group consisting of laponite, bentonite, montmorillonite, beidelite, hectorite, saponite and stevensite. More particularly, the clay may be laponite.

The weakly acidic pharmaceutically active ingredient of the inventive formulation may be selected from the group consisting of captopril, diclofenac, enalapril, furosemide, ketoprofen, phenobarbital, naproxen, ibuprofen, lovstatin, penicillin G, piroxicam and ranitidine.

More particularly, the pharmaceutical formulation of the invention may comprise:
(a) in amounts from about 40% (w/w) to about 98% (w/w);
(b) glycerin in amounts from about 20% (w/w) to about 60% (w/w);
(c) clay in amounts from about 0.25% (w/w) to about 0.5% (w/w);
(d) water soluble cellulose ethers in amounts from about 0.8% (w/w) to about 2.0% (w/w);
(e) an effective amount of a pharmaceutically active ingredient.

In a further embodiment, the pharmaceutical formulation of the invention has carboxymethyl cellulose as the water soluble cellulose ether.

The pharmaceutical formulation of the present invention, comprising a weakly acidic a pharmaceutically active ingredient, a liquid base, a clay and a water soluble cellulose ether may further comprise propylene glycol. The pharmaceutical formulation may have propylene glycol in amounts of about 5% (w/w).

Additionally, the pharmaceutical formulation comprising a weakly acidic a pharmaceutically active ingredient, a liquid base, a clay and a water soluble cellulose ethers may further comprise sorbitol in amounts of about 5% (w/w).

DETAILED DESCRIPTION

The pharmaceutical formulations of the present invention exhibit spill resistant characteristics. A spill-resistant pharmaceutical formulation according to the invention begins to spill from a spoon bowl during test periods of vibrations, inversion, and tilting, but slowly enough to conform with practical time limits between dispensing and ingesting, and quickly enough to enable the product to be readily consumed from a spoon bowl.

Only certain pharmaceutical formulations can be prepared that have the physico-chemical and rheological characteristics of a spill resistant pharmaceutical formulation. The physio-chemical and rheological characteristics of spill-resistant formulations are described in U.S. Pat. Nos. 6,071,523, 6,355,258, 6,399,079 and 6,656,482.

The physico-chemical and rheological characteristics which impart the spill resistant consistency of the formulation, permit the composition to be squeezed into a spoon from a container with light manual pressure, to spread and level in a spoon bowl quickly enough for accurate measurement (typically in about 1-5 seconds at room temperature), and to remain in the spoon bowl long enough to permit administration without spilling particularly under difficult circumstances such as encountered with dispensing to children, or by the elderly. The elderly typically exhibit impaired movement either due to arthritis or tremors e.g., essential tremor. The spill-resistant pharmaceutical formulation for oral administration from a squeezable container comprises a per-unit dose effective amount of a pharmaceutical agent in a suitable vehicle comprising a liquid base and thickening or viscosity agents.

The formulation consists of mutually compatible components as described below. The formulation has the following properties:
a) a viscosity within the range of about 5000 to about 25,000 cps using a Brookfield Viscometer with a 'C' spindle with Helipath movement at a spindle speed of 20 rpm and 20-25 degree centigrade;
b) a viscometric yield value of a semi-solid; a spill-resistant consistency permitting the composition to be squeezed by light manual pressure through a channel of about 1-5 mm;
c) the yield value allows the formulation to spread in a spoon bowl sufficiently quickly for accurate measurement (1-5 seconds), and to remain in the spoon bowl without spilling for several seconds (15-60) on spoon inversion (180 degrees) and tilting at up to 90 degrees, preferably up to 30 seconds at 30 degrees, and for at least 50 seconds upon spoon vibration. The shaking, tilting and inversion tests are performed on an experimental platform as described in detail in U.S. Pat. No. 6,071,523;
d) homogeneity such that the components do not separate under conditions of use;
e) and a storage stability such that the foregoing properties are retained for at least two months of storage at accelerated stability conditions of elevated temperature and humidity;

A spill-resistant formulation according to the invention begins to spill from a spoon bowl during test periods of vibrations, inversion, and tilting, but slowly enough to conform with practical time limits between dispensing and ingesting, and quickly enough to enable the product to be readily consumed from a spoon bowl by a patient. The spill resistant formulation is easy and accurate while dispensing and dosing to a 5.0 mL teaspoon.

The Brookfield viscosity of the pharmaceutical formulation falls within the range of about 5,000 centipoises (cps) to about 25,000 centipoises (cps) at room temperature. Viscosity is measured using a Brookfield Viscometer with a 'C' spindle with Helipath movement at 20 RPM and 20-25 degree centigrade, or equivalent. Viscosity decreases slightly with increasing temperature. Although spill resistant properties correlate with viscosity, they are not necessarily directly linked to viscosity, so that compositions that fall within the target viscosity range may nevertheless lack spill resistance.

The flow quality of the formulation is a non-Newtonian, pseudoplastic and time independent fluidity wherein the viscosity of the non-solid gel decreases with increasing shear rate. The flow quality behavior is fully reversible, and is indicative of Bingham behavior. Spill resistant pharmaceutical formulations are non-Newtonian and time independent fluids. Non-Newtonian refers to a fluid whose behavior departs from that of an ideal Newtonian fluid. These fluids have different viscosities at different shear rates and fall under two groups: time independent and time dependent. Time independent fluids are those for which the rate of shear at any point in the fluid is some function of the shear stress at that point and depends on nothing else. These fluids have a constant viscosity value at a given shear rate. The viscosities do not change with time. (McGraw-Hill Encyclopedia of Science & Technology, $6^{th}$ edition, 1987, Volume 12, pages 57-60).

Viscometric yield value means the ease of administration comprising (a) extrudability under light manual pressure from a squeezable container or a proxy (e.g. a syringe with a 5 mm orifice), and (b) spreadability in a spoon bowl measured by extruding the formulation into a spoon bowl and determining whether the material spreads to the edges of the spoon bowl. Yield value is the initial resistance to flow under stress. Yield value is a measurable quantity similar to, but not dependent on, viscosity. The yield value of the spill resistant pharmaceutical formulations are from about 5 to about 200 $D/cm^2$ exhibits and exhibit Bingham behavior. Bingham plastics exhibit a yield stress, which is the stress that must be exceeded before flow starts, thereafter the rate-of-shear curve is linear. There are other materials that also exhibit a yield stress, but the flow curve is thereafter not linear. These are usually called generalized Bingham plastics. A Bingham flow requires an initial stress, the yield value, before it starts to flow. Once the yield value is exceeded and flow begins a Bingham fluid may display Newtonian, pseudoplastic or dilatant flow characteristics.

The spill resistant pharmaceutical formulations of the present application have a pseudoplastic fluid's ratio of shear stress to the rate of shear, which may be termed the apparent viscosity, falls progressively with shear rate. The decrease in viscosity with an increase in shear rate is also known as shear thinning. This phenomenon of shear thinning is characteristic of formulations of asymmetric particles or solution of polymers such as cellulose derivatives. The viscosity of the spill resistant pharmaceutical formulation decreases with increasing shear rate, e.g., increasing the spindle speed. The desirable spill resistant properties occur at a viscosity greater than about 5,000 cps. The product spreads quickly at viscosity less than about 25,000 cps. Thus, spill resistance and spreading characteristics are desirable in this viscosity range. The viscosity of the formulation increases with decrease in temperature and decreases with increase in temperatures. However, these changes in the viscosity and correlated spill resistant characteristics are reversible, so that the original formula viscosity is obtained when temperature returns to room temperature (~23° C.; broadly 19° C. to about 29° C.).

The composition has some or all of the following qualities. First, if the formulation is a suspension, the active ingredient is uniformly dispersed in the vehicle. The crystalline stability of the formulation is such that the active ingredient does not exhibit excessive crystalline growth or dissolution so that the particles stay within a target particle size range. The pharmaceutically active ingredient remains suspended indefinitely without agitation, that is without stirring or shaking. The uniformity of the formulation provides for consistent dosing and increased shelf life of the product, as the active ingredient remains uniform per dose administered, and does not fall out of solution or separate from the suspension.

The antimicrobial activity of the spill resistant pharmaceutical formulations meet standard microbial challenge requirements, such as those described by the USP. The microbial challenge requirements may be either due to preservatives or to a low water activity (about 0.60 to about 0.84). Some preferred preservatives may be benzoic acid, sodium benzoate, sorbic acid, potassium sorbate, propionic acid, sodium propionate, ethyl alcohol, methylparaben, ethylparaben, propylparaben, and butylparaben. Other preservatives known in the art, may be used. These formulations may be alcohol-free to avoid complications from using alcohol. The spill resistant formulations are palatable and have an acceptable taste and good mouthfeel.

Mutual compatibility of the components means that they do not separate in preparation and storage of the formulation for the equivalent of two years at room temperature (as indicated by six-months accelerated stability testing at 40° C. and 75% relative humidity). Storage stability means that the materials do not lose their desirable properties during storage for the same period. Preferred compositions do not exhibit a drop in viscosity of more than 50% or an increase in viscosity of more than 100% during that period. Additionally, the components are mutually compatible in that they do not interfere with the bioactivity of the pharmaceutical agent or physical properties of the vehicle. The components do not separate and retain the desired physico-chemical properties.

The pharmaceutically active ingredient of the spill-resistant pharmaceutical formulation of the present application will have a pKa that will not easily dissolve or disperse in a neutral pH. The solution or suspension will be titrated to a pH of between 3.0 to 6.0 or, alternatively, from 7.5 to 10.0. The inventive formulation may include a buffer that will resist change of the pH on adding acid or alkali, or on dilution with a solvent. Examples of some commonly used pharmaceutical buffer systems are $NH_4Cl$, diethanolamine, triethanolamine, borate, carbonate, phosphorate, glutamate, succinate, malate, tartarate, glutarate, citrate, acetic acid, benzoate, lactate, glycerate, and gluconate. The pharmaceutical formulation thus formed will have enhanced stability because the pH is controlled in a narrow range.

Many drugs are weak acids or bases (Goodman & Gilman's, The *Pharmacological Basis of Therapeutics*, $10^{th}$ Edition, 2001). Acids are substances that are capable of donating protons and bases are substances that are capable of accepting protons. The strength of an acid or base varies with the solvent. The strength of an acid depends not only on its ability to give up a proton, but also on the ability of the solvent to accept the proton. The pH of the drug in aqueous solution will depend upon the disassociation constant of the drug in the solution. Weak acids are soluble in basic aqueous solutions, whereas weak bases are more soluble in acidic aqueous solution. Weak acids and weak bases are discussed in detail in *Physical Pharmacy*. 4th Edition, ed. Alfred Martin, Lippincott Williams & Wilkins, 1993, Chapter 7.

Examples of pharmaceutically active ingredients which may be suitable for use in the present dosage forms includes, without limitation, analgesics, anti-inflammatories, antipyretics, antibiotics, antimicrobials, laxatives, anorexics, antihistamines, antiasthmatics, antidiuretics, antiflatuents, antimigraine agents, antispasmodics, sedatives, antihyperactives, antihypertensives, tranquilizers, decongestants, beta blockers; peptides, proteins, oligonucleotides and other substances of biological origin, and combinations thereof.

Examples of pharmaceutically active ingredients that are weak bases include, acyclovir, atenolol, atropine, ciprofloxacin, dilitiazem, diphenhydramine, diphenhydramine HCl, epinephrine, ephedrine, glucosamine, glucosamine sulfate, hydrochlorothiazide, loratadine, metoprolol, nortriptyline, phenytoin, propoxyphene, propranolol, prednisolone, terfenadine, tetracycline, pseudoephedrine and mixtures thereof.

Examples of pharmaceutically active ingredients that are weak acids include, captopril, diclofenac, enalapril, furosemide, ketoprofen, phenobarbital, naproxen, ibuprofen, lovstatin, penicillin G, piroxicam and ranitidine.

The pharmaceutical formulation described herein has a therapeutically orpharmacologically effective amount of either a water-soluble or water insoluble pharmaceutically active ingredient. By therapeutically and pharmacologically effective, it is meant the active ingredient is present in enough quantity, or concentration, to cause a response in a physiologic system. It would be clear to one skilled in the art to determine the pharmaceutically effective amount using known drug therapies, e.g. *The Physicians Desk Reference* 2004. Thomson Healthcare; 58th Bk&Cr edition.

Additional components of the pharmaceutical formulation may include one or more of the following: surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; pharmaceutically acceptable polymeric or hydrophobic materials as well as other components. Ethylenediaminetetraacetic acid (EDTA) may be used as a chelating agent because it forms stable water-soluble complexes with alkaline earth and heavy metal ions.

The spill resistant pharmaceutical formulation contain thickening, or viscosity, agents which maintain the yield value of the formulation. Surprisingly, inorganic clays provide a stable vehicle at both an acidic pH as well as basic pH for the spill resistant formulations. The inorganic clay may be selected from the group consisting of bentonite, laponite, montmorillonite, beidelite, hectorite, saponite and stevensite, or mixtures thereof. Hectorites and bentonites, both synthetic and natural, may be used as thickening agents. Examples of a thickening, or viscosity, agent used to increase the viscosity of the formulation is a synthetic hectorite clay that imparts high shear thinning and thixotropic rheology to water based systems, such as laponite. Hectorites having extra-small platelet size of 25×1 nanometer allows the formation of clear gels rather than opaque gel. The addition of small quantities of electrolytes allows for the formulation of thixotropic clear gels. Hectorite clays are magnesium silicates with a layered structure and are marketed as granular, free flowing white powders. When dispersed in water the hectorites form thixotropic gels, or, if the sol forming grades are used, clear stable sols. These sols can be changed into thixotropic gels if or when required. The gel systems produced form dispersions of these products in Bingham fluids.

In order to create a spill resistant formulation, various cellulose derivatives were experimented with in combination with the inorganic clays to impart a yield value to the gel. Hydroxypropyl cellulose (HPC), Hydroxypopylmethyl cellulose (HPMC) and Microcrystalline cellulose (also known as sodium carboxymethylcellulose (CMC)) were tested. All of the cellulose/clay combinations possessed gel like properties in the test formulations. However, the HPC/clay and HPMC/clay compositions had some undesirable physical properties, i.e. the gels were stringy and/or not clear. Additionally, the gels did not perform well on the spill resistant tests. The compositions tended to spread too quickly, or too slowly. These results are demonstrated by Sample B-P in Table 1 and Table 2, below.

In contrast, the CMC/clay combination produced a clear gel with spill resistant like properties. The CMC/laponite combination will produce a gelling agent that facilitates the formulation of basic active agents to produce spill resistant gels at lower pH (from about pH 3.5 to about pH 5.5) and with acidic active agents at higher pH (from about pH 7 to about pH 10).

The pharmaceutical formulation may also comprise a carrier for the pharmaceutically active ingredient and the variety of other excipients. For example, propylene glycol may be used in amounts up to fifty (50) percent (w/w). Other excipients that may be used include glycerin and sorbitol. Either glycerin or sorbitol may be used in amounts of up to about fifty (50) percent (w/w). Purified water is also added to the pharmaceutical formulation.

The pharmaceutical formulation may also comprise organoleptic components, which impart desirable sensory characteristics including taste, color, and smell. The organoleptic component may comprise a high intensity sweetener that improves sensory appeal such as sucralose liquid concentrate. These components may also include coloring agents that provide desired coloring to the formulation. Flavoring agents such as cherry flavor or a concentration of berry flavor, and taste masking agents may be included.

Any conventional technique may be used for the preparation of pharmaceutical formulations according to the invention. In general, preparation includes bringing the active ingredient into association with a carrier or one or more other additional components, and then, if necessary or desirable, shaping or packaging the product into a desired single- or multi-dose unit. The active ingredient may be contained in a formulation that provides quick release, sustained release or delayed release after administration to the patient.

The pharmaceutical compositions may be prepared, packaged, or sold in formulations suitable for oral, parenteral and topical administration. Other contemplated formulations include nanoparticles, liposomal preparations, resealed erythrocytes containing the active ingredient, and immunologically-based formulations. A pharmaceutical composition of the invention may be prepared, packaged, or sold in bulk, as a single unit dose, or as a plurality of single unit doses. A unit dose is a discrete amount of the pharmaceutical composition comprising a predetermined amount of the active ingredient. The amount of the active ingredient in each unit dose is equal to the total amount of the active ingredient which would be administered or a convenient fraction of a total dosage amount such as, for example, one-half or one-third of such a dosage.

Although the descriptions of pharmaceutical compositions provided herein are principally directed to pharmaceutical compositions which are suitable for administration to humans, it will be understood by the skilled artisan, based on this disclosure, that such compositions are generally suitable for administration to any mammal. Preparation of compositions suitable for administration to various animals is well understood, and the ordinarily skilled veterinary pharmacologist can design and perform such modifications with routine experimentation based on pharmaceutical compositions for administration to humans.

EXAMPLES

Example 1

The spill resistant-like properties of the hectorite gel, laponite, were investigated. Laponite gel samples were compounded either with carbomer, sodium carboxymethylcellulose (CMC), hydroxypropylcellulose (HPC) and hydroxypropyl methylcellulose (HPMC) as described below:
A. weigh and measure clay and water to a stainless steel vessel and mix until a clear solution is formed. Crystalline sorbitol is added after the clay dissolves, and the solution is mixed until a clear solution is formed;
B. add sodium carboxymethylcellulose (CMC), hydroxypropylcellulose (HPC), or hydroxypropyl methylcellulose (HPMC) to solution A until a uniform dispersion forms;
C. add glycerin, propylene glycol and citric acid, to dispersion B and mix until a uniform dispersion is achieved.

Examples of spill resistant formulations using a combination of cellulose and laponite thickening agents, in varying quantities, are given in Table 1. The experimental laponite containing spill resistant formulations described in Table 1, containing either a) carbomer, b) sodium carboxymethylcellulose (CMC), c) hydroxypropylcellulose (HPC) or d) hydroxypropyl methylcellulose (HPMC) were compared against a control spill resistant formulation containing the active ingredient, Pseudoephedrine, and the thickening agent, carbomer (as described in published U.S. Patent Publication No. US20030235618A1, hereby incorporated by reference).

As shown in Table 2 the control spill resistant preparation containing pseudoephedrine exhibited the following characteristics: (i) a viscosity of 11,350 cps; (ii) a spreading of 2 seconds; (iii) an inversion time of greater than 60 seconds; (iv) a tilting time of greater than 60 seconds; and (v) a shaking time of 60 seconds.

As observed, all of the experimental laponite pharmaceutical formulation samples formed gels when mixed with water. However, the HPMC/laponite gels were translucent and did not meet the spill resistant criteria of the testing (see Tables 1 and 2—Samples B and C).

HPC/laponite formulations tended to be more filamentous than the gels provided by other cellulose ethers. However, it was observed that 2% HPC/0.5% laponite (Table 1 sample G) did provide for an acceptable spill resistant composition (Table 2, Sample G).

A synergistic rheology was perceived with the CMC/laponite gels (see Tables 1 and 2 samples M-T). Experimentally, increasing the amount of the CMC in the formulation appeared to have a detrimental effect on the spill resistant characteristics. Sample M containing 1.5% CMC/0.25% laponite and Sample N containing 2% CMC/0% laponite, both resulted in smooth clear gels that either did not spread in the spoon, or fell off the spoon too quickly on inversion (see example M and N; Tables 1 and 2).

Specifically, the spill resistant gels exhibited the following characteristics: (i) a viscosity between 6,800 cps (sample G) and 15,240 cps (sample T); (ii) a spreading in the spoon bowl of less than 4 seconds; (iii) an inversion time of greater than 60 seconds; (iv) a tilting time of greater than 60 second; and (v) a shaking time of greater than or equal to about 50 seconds.

Spill Resistant formulations existed at both basic pH (samples G and K), and acidic pH (samples L, O-T). The pH values of all the samples without the addition of citric acid were in the ranges of 9.26 to 9.89. It is possible to increase the pH to greater than 9.9 with the addition of NaOH, or other suitable bases. Citric acid was added to the Samples J, L, O, P, Q, R, S, and T to reduce the pH to an acidic value. No adverse effect was observed by the addition of the acid.

TABLE 1

Compositions containing carbomer, sodium carboxymethylcellulose (CMC), hydroxypropylcellulose (HPC), hydroxypropyl methylcellulose (HPMC), respectively.

| Sample | Water (%) | Glycerin (%) | Laponite (%) | Other Ingredient (%) | Observations |
|---|---|---|---|---|---|
| Control 0.26% Pseudoephedrine | 33.38 | 50 | 0 | 0.33 (carbomer) 0.27 (NaOH) 3.0 (sucralose) | Smooth clear gel |
| A | 38.5 | 50.0 | 1.5 | 0.2 (carbomer) 0.1 (NaOH) 5.0 (propylene glycol) | Smooth clear gel |
| B | 57.0 | 40.0 | 1.5 | 1.5 (HPMC) | Aerated translucent smooth gel |
| C | 98.0 | 0 | 0.5 | 1.5 (HPMC) | Translucent smooth gel |
| D | 58.5 | 40.0 | 0.5 | 1.0 (HPC) | Translucent gel with slimy filament texture |
| E | 58.0 | 40.0 | 0.5 | 1.5 (HPC) | Translucent gel with slimy filament texture |
| F | 58.0 | 40.0 | 0.5 | 1.5 (HPC) 0.04 (Citric acid) | Translucent gel with slimy filament texture |
| G | 97.5 | 0 | 0.5 | 2.0 (HPC) | Aerated viscous translucent gel |
| H | 98.0 | 0 | 0 | 2.0 (HPC) | Smooth soft clear gel |
| I | 98.0 | 0 | 0.5 | 1.5 (CMC) | Rigid smooth clear gel, very thixotropic |
| J | 98.0 | 0 | 0.5 | 1.5 (CMC) 0.04 (Citric acid) | Rigid smooth clear gel, very thixotropic |
| K | 98.5 | 0 | 0.5 | 1.0 (CMC) | Rigid smooth clear gel, very thixotropic |

TABLE 1-continued

Compositions containing carbomer, sodium carboxymethylcellulose (CMC), hydroxypropylcellulose (HPC), hydroxypropyl methylcellulose (HPMC), respectively.

| Sample | Water (%) | Glycerin (%) | Laponite (%) | Other Ingredient (%) | Observations |
|---|---|---|---|---|---|
| L | 98.5 | 0 | 0.5 | 1.0 (CMC) <br> 0.04 (Citric acid) | Rigid smooth clear gel, very thixotropic |
| M | 98.3 | 0 | 0.25 | 1.5 (CMC) | Smooth clear gel |
| N | 98.0 | 0 | 0 | 2.0 (CMC) | Smooth soft clear gel |
| O | 78.5 | 20.0 | 0.5 | 1.0 (CMC) <br> 0.04 (Citric acid) | Smooth clear gel |
| P | 58.8 | 30 | 0.25 | 0.8 (CMC) <br> 5.0 (Propylene glycol) <br> 5.0 (Sorbitol) <br> 0.2 (Citric acid) | Smooth clear gel |
| Q | 58.5 | 40.0 | 0.5 | 1.0 (CMC) <br> 0.04 (Citric acid) | Smooth clear gel |
| R | 58.5 | 40.0 | 0.5 | 1.0 (CMC) <br> 0.14 (Citric acid) | Smooth clear gel, palatable taste, slightly starchy mouth-feel |
| S | 58.3 | 40 | 0.25 | 1.3 (CMC) <br> 0.2 (Citric acid) | Smooth clear gel |
| T | 58.5 | 30 | 0.25 | 1.1 (CMC) <br> 5.0 (Propylene glycol) <br> 5.0 (Sorbitol) <br> 0.2 (Citric acid) | Smooth clear gel |

TABLE 2

Spill Resistant Formulations

| Sample | pH | Viscosity[1] (cps) | Spreading (sec.) | Inversion (sec.) | Tilting (sec.) | Shaking (sec.) | Spill Resistant Characteristics |
|---|---|---|---|---|---|---|---|
| Control 0.26% Pseudoephedrine | 6.10 | 11350 | 2 | >60 | >60 | >60 | Yes |
| A | 5.82 | 10540 | 1.5 | >60 | >60 | 51 | Yes |
| B | 9.60 | 29250 | 4 | >60 | >60 | >60 | No |
| C | 9.89 | 8130 | 1.5 | 8 | 20 | >60 | No |
| D | 9.26 | 10590 | 1.5 | 5 | 11 | 6 | No |
| E | 9.31 | 27170 | 3 | 36 | >60 | >60 | No |
| F | 3.49 | 22230 | 2 | 16 | 36 | >60 | No |
| G | 9.55 | 6800 | 2 | >60 | >60 | >60 | Yes |
| H | 6.09 | 8250 | 1.5 | 5 | 9 | >60 | No |
| I | 9.55 | 22540 | >4 | >60 | >60 | >60 | No |
| J | 5.61 | 21390 | >4 | >60 | >60 | >60 | No |
| K | 9.57 | 12290 | 4 | >60 | >60 | >60 | Yes |
| L | 5.43 | 11540 | 4 | >60 | >60 | >60 | Yes |
| M | 9.40 | 19920 | >4 | >60 | >60 | >60 | No |
| N | 6.65 | 12320 | 1.5 | 19 | 29 | >60 | No |
| O | 6.32 | 14530 | 4 | >60 | >60 | >60 | Yes |
| P | 4.37 | 9550 | 1.5 | >60 | >60 | 51 | Yes |
| Q | 6.21 | 12680 | 2 | >60 | >60 | >60 | Yes |
| R | 4.78 | 11820 | 2 | >60 | >60 | >60 | Yes |
| S | 4.40 | 16780 | 2.5 | >60 | >60 | >60 | Yes |
| T | 4.50 | 15240 | 2 | >60 | >60 | >60 | Yes |

[1]Brookfield viscometer Vis02, Spindle C @ 20 rpm at RT.

Example 2

Acyclovir is an active agent that is a weak base, and is thus poorly soluble at the optimal pH range for a carbomer based spill resistant formulation. A more acidic pH for the pharmaceutical formulation is desired to achieve a stable, spill resistant acyclovir formulation with the proper viscosity. We anticipate that a pH of 3.0 to 3.5 would be desirable for formulation of the suspension. A suspension of 200 mg/ml of the antiviral agent acyclovir will be used in a spill resistant pharmaceutical formulation containing CMC/clay as the thickening agent. As a formulation, the following ingredients will be used to form a spill resistant 200 mg/5 ml acyclovir suspension.

TABLE 3

Proposed 200 mg/5 ml Acyclovir Spill Resistant Formulation

| Ingredients | Sample A % (w/w) |
|---|---|
| Water | 30.93 |
| Glycerin | 50.0 |
| Polyethylene glycol 1000 | 15.0 |
| Laponite | 0.25 |
| Carboxymethylcellulose | 1.1 |
| Sucralose | 0.5 |
| Citric Acid | 0.4 |
| Initial viscosity at 23° C., cps | 11000 |

Stabilizers, anti-microbials, organoleptic and other excipients will be added as needed. The formulation will have the spreading, tilting, shaking and consistency of a spill resistant formulation, as shown in Table 4.

TABLE 4

Spill Resistant Characteristics for an Acyclovir Suspension

| Lot # | pH | Viscosity[1] (cps) | Spreading (sec.) | Inversion (sec.) | Tilting (sec.) | Shaking (sec.) |
|---|---|---|---|---|---|---|
| Acyclovir | 3.25 | 11000 | 2 | >60 | >60 | >60 |

Example 3

Stability Testing

Stability testing will done at 0 months, 6 months, 12 months and 18 months post manufacturing of Exhibit Samplees of an Acyclovir Suspension Formulation. The following tests will be done:
- A. Description of physical properties of product.
- B. pH of the undiluted product will measured using pH-meter.
- C. Viscosity will be measured using a Brookfield Viscometer with a 'T-C' spindle 20 RPM at 20-25° C.
- D. Impurities will be measured by reverse-phase HPLC, using a C column with an organic mobile phase, eluting at appropriate times for the column wash, with detection by UV absorption. Samples will be prepared for analysis by dissolving of product in the sample solvent and subsequent dilution in the sample solvent to desirable concentration. Retention time of preservatives, active agents and any identified impurities will be calibrated.
- E. Bottle uniformity is a measure of the any active agent at the top, middle and bottom levels of the bottle. Amount of pharmaceutically active ingredients will be measured by HPLC as explained above (step D).
- F. Dissolution—amount of dissolved active (% label claim) will be adopted directly from the USP Dissolution procedure. Dissolution testing will measure the amount of pharmaceutical active ingredient dissolved in 60 minutes in a dissolution apparatus using a spindle at 50 rpm (revolutions per minute) at 37° C. A dissolution apparatus (Distek Inc., North Brunswick, N.J.), equipped with 6 to 8 vessels immersed in a water bath and maintained at 37±0.5° C., and individual spindles for each vessel will be employed for the testing. Samples will be taken by syringe at regular intervals from each vessel and measured by HPLC.

An example of desired stability data is given in Table 5.

TABLE 5

Stability Data

| Parameter | 0 Months | 6 Months | 12 Months | 18 Months | 24 Month |
|---|---|---|---|---|---|
| Description | Orange, opaque, viscous, jellylike material with characteristic berry odor | Orange, opaque, viscous, jellylike material with characteristic berry odor | Orange, opaque, viscous, jellylike material with characteristic berry odor | Orange, opaque, viscous, jellylike material with characteristic berry odor | Orange, opaque, viscous, jellylike material with characteristic berry odor |
| pH | 3.2 | 3.2 | 3.2 | 3.2 | 3.2 |
| Viscosity | 11000 cps | 11000 cps | 11000 cps | 11000 cps | 11000 cps |
| Acyclovir (mean of Bottle Uniformity) | 99.1% | 101.5% | 101.9% | 102.1% | 102.1% |
| Bottle Uniformity (with relative standard deviation) | Top: 99.1% Middle: 99.0% Bottom: 99.2% % RSD 0.1% | Top: 101.5% Middle: 102.6% Bottom: 101.9% % RSD 1.3% | Top: 100.6% Middle: 101.8% Bottom: 103.2% % RSD 1.3% | Top: 98.9% Middle: 102.2% Bottom: 105.2% % RSD 3.1% | Top: 98.9% Middle: 102.2% Bottom: 105.2% % RSD 3.1% |
| Bottle Uniformity (with relative standard deviation) | Top: 99.1% Middle 99.0% Bottom: 99.2% % RSD 0.1% | Top: 101.5% Middle: 102.6% Bottom: 101.9% % RSD 1.3% | Top: 100.6% Middle: 101.8% Bottom: 103.2% % RSD 1.3% | Top: 98.9% Middle: 102.2% Bottom: 105.2% % RSD 3.1% | Top: 98.9% Middle: 102.2% Bottom: 105.2% % RSD 3.1% |
| Butylparaben Assay | 103.1% | 104.4% | 104.6% | 103.4% | 103.4% |
| Dissolution (vessels ($V_{1-6}$)) | $V_1$ = 96% $V_2$ = 96% $V_3$ = 96% $V_4$ = 97% $V_5$ = 102% $V_6$ = 99% | $V_1$ = 102% $V_2$ = 102% $V_3$ = 102% $V_4$ = 100% $V_5$ = 101% $V_6$ = 101% | $V_1$ = 102% $V_2$ = 102% $V_3$ = 102% $V_4$ = 102% $V_5$ = 102% $V_6$ = 102% | $V_1$ = 102% $V_2$ = 102% $V_3$ = 102% $V_4$ = 102% $V_5$ = 102% $V_6$ = 102% | $V_1$ = 102% $V_2$ = 102% $V_3$ = 102% $V_4$ = 102% $V_5$ = 102% $V_6$ = 102% |
| Microbiological Examination | Less than 10 microorganisms/g (no *Salmonella* or *E. Coli*) | Less than 10 microorganisms/g (no *Salmonella* or *E. Coli*) | Less than 10 microorganisms/g (no *Salmonella* or *E. Coli*) | Less than 10 microorganisms/g (no *Salmonella* or *E. Coli*) | Less than 10 microorganisms/g (no *Salmonella* or *E. Coli*) |
| Impurity 1 | Not detected | Less than 0.050% | Not detected | Not detected | Not detected |
| Impurity 2 | Less than 0.050% | Less than 0.050% | Less than 0.050% | Not detected | Not detected |
| Total Impurities | Less than 0.050% | Less than 0.050% | Less than 0.050% | Not detected | Not detected |

The invention claimed is:

1. A pharmaceutical formulation, comprising a weakly basic pharmaceutically active ingredient, a liquid base, clay and at least one water soluble cellulose ether, wherein the pharmaceutical formulation exhibits spill resistant characteristics and wherein the viscosity of the pharmaceutical formulation ranges from about 5,000 cps to about 25,000 cps when measured using a Brookfield viscometer at a spindle speed of 20 rpm.

2. The pharmaceutical formulation of claim 1, wherein the pH of the pharmaceutical formulation is between about 3.0 and about 6.5.

3. The pharmaceutical formulation of claim 1, wherein the viscosity of the pharmaceutical formulation ranges from about 5,000 cps to about 17,000 cps.

4. The pharmaceutical formulation of claim 1, wherein the weakly basic pharmaceutically active ingredient, the liquid base, the clay and the water soluble cellulose ether do not separate into separate components after storage at room temperature for at least twenty-four months.

5. The pharmaceutical formulation of claim 1, wherein the weakly basic pharmaceutically active ingredient, the liquid base, the clay and the water soluble cellulose ether do not separate under accelerated stability conditions for at least 6 months.

6. The pharmaceutical formulation of claim 1, wherein the liquid base is selected from the group consisting of glycerin, propylene glycol, sorbitol and mixtures thereof.

7. The pharmaceutical formulation of claim 1, wherein the clay is selected from the group consisting of laponite, bentonite, montmorillonite, beidelite, hectorite, saponite, stevensite and mixtures thereof.

8. The pharmaceutical formulation of claim 1, wherein the weakly basic pharmaceutically active ingredient is selected from the group consisting of acyclovir, atenolol, atropine, ciprofloxacin, dilitiazem, diphenhydramine, diphenhydramine HCl, epinephrine, ephedrine, glucosamine, glucosamine sulfate, hydrochlorothiazide, metoprolol, nortriptyline, phenytoin, propoxyphene, propranolol, terfenadine, tetracycline, pseudoephedrine and mixtures thereof.

9. The pharmaceutical formulation of claim 1, comprising:
    (a) from about 20% (w/w) to about 98% (w/w) water;
    (b) from about 20% (w/w) to about 60% (w/w) glycerin;
    (c) from about 0.25% (w/w) to about 0.5% (w/w) clay;
    (d) from about 0.8% (w/w) to about 2.0% (w/w) of one or more water soluble cellulose ethers; and
    (e) an effective amount of at least one pharmaceutically active ingredient.

10. The pharmaceutical formulation of claim 9, wherein the water soluble cellulose ether is carboxymethyl cellulose.

11. A pharmaceutical formulation, comprising a weakly acidic pharmaceutically active ingredient, a liquid base, clay and at least one water soluble cellulose ether, wherein the pharmaceutical formulation exhibits spill resistant characteristics and wherein the viscosity of the pharmaceutical formulation ranges from about 5,000 cps to about 25,000 cps when measured using a Brookfield viscometer at a spindle speed of 20 rpm.

12. The pharmaceutical formulation of claim 11, wherein the pH of the pharmaceutical formulation is between about 7.5 and about 10.

13. The pharmaceutical formulation of claim 11, wherein the viscosity ranges from about 5,000 cps to about 17,000 cps.

14. The pharmaceutical formulation of claim 11, wherein the weakly acidic pharmaceutically active ingredient, the liquid base, the clay and the water soluble cellulose ether do not separate into separate components after storage at room temperature for at least twenty four months.

15. The pharmaceutical formulation of claim 11, wherein the weakly acidic pharmaceutically active ingredient, the liquid base, the clay and the water soluble cellulose ether do not separate under accelerated stability conditions for at least 6 months.

16. The pharmaceutical formulation of claim 11, wherein the liquid base is selected from the group consisting of glycerin, propylene glycol, sorbitol and mixtures thereof.

17. The pharmaceutical formulation of claim 11, wherein the clay is selected from the group consisting of laponite, bentonite, montmorillonite, beidelite, hectorite, saponite, stevensite and mixtures thereof.

18. The pharmaceutical formulation of claim 11, wherein the weakly acidic pharmaceutically active ingredient is selected from the group consisting of captopril, diclofenac, enalapril, furosemide, ketoprofen, phenobarbital, naproxen, ibuprofen, lovastatin, penicillin G, piroxicam, ranitidine and mixtures thereof.

19. The pharmaceutical formulation of claim 11, comprising:
    (a) from about 20% (w/w) to about 98% (w/w) water;
    (b) from about 20% (w/w) to about 60% (w/w) glycerin;
    (c) from about 0.25% (w/w) to about 0.5% (w/w) clay;
    (d) from about 0.8% (w/w) to about 2.0% (w/w) of one or more water-soluble cellulose ethers; and
    (e) an effective amount of at least one pharmaceutically active ingredient.

20. The pharmaceutical formulation of claim 19, wherein the water-soluble cellulose ether is carboxymethyl cellulose.

* * * * *